United States Patent
Reynolds et al.

(10) Patent No.: US 7,937,981 B2
(45) Date of Patent: May 10, 2011

(54) PROCESS FOR TREATING METAL ALLOY SURGICAL NEEDLES TO IMPROVE BENDING STIFFNESS

(75) Inventors: Eugene D. Reynolds, Avon by the Sea, NJ (US); Robert Maurer, Belle Mead, NJ (US); Michael Nordmeyer, Pittstown, NJ (US); Frank R. Cichocki, Easton, PA (US); Lester E. Schaible, Hillsborough, NJ (US); Daniel J. Smith, Dayton, NJ (US)

(73) Assignee: Ethicon, Inc., Somerville, NJ (US)

( * ) Notice: Subject to any disclaimer, the term of this patent is extended or adjusted under 35 U.S.C. 154(b) by 732 days.

(21) Appl. No.: 11/957,629

(22) Filed: Dec. 17, 2007

(65) Prior Publication Data

US 2009/0157117 A1 Jun. 18, 2009

(51) Int. Cl.
*B21D 11/00* (2006.01)
*B21G 3/18* (2006.01)

(52) U.S. Cl. ............ 72/306; 72/214; 72/215; 72/702; 163/5

(58) Field of Classification Search ........... 72/31.04, 72/31.05, 127, 135, 137, 166, 168, 169, 306, 72/307, 702, 125, 187, 188, 190, 191, 196, 72/214, 215; 140/80, 102, 104; 163/1, 5; 148/668, 673
See application file for complete search history.

(56) References Cited

U.S. PATENT DOCUMENTS

| | | | | |
|---|---|---|---|---|
| 1,670,292 A | * | 5/1928 | Koref et al. | 148/673 |
| 3,038,475 A | | 6/1962 | Orcutt | |
| 3,238,942 A | | 3/1966 | Lincoff | |
| 3,459,018 A | * | 8/1969 | Miller | 72/14.8 |
| 4,025,044 A | * | 5/1977 | Goderbauer | 238/349 |
| 4,602,636 A | | 7/1986 | Noiles | |
| 4,989,439 A | * | 2/1991 | Ewert et al. | 72/372 |
| 5,415,707 A | * | 5/1995 | Bendel et al. | 148/423 |
| 5,649,961 A | | 7/1997 | McGregor et al. | |
| 5,676,008 A | * | 10/1997 | Morin | 72/129 |
| 6,592,559 B1 | | 7/2003 | Pakter et al. | |
| 2006/0058843 A1 | | 3/2006 | Mashiko et al. | |
| 2008/0300552 A1 | * | 12/2008 | Cichocki et al. | 604/239 |

FOREIGN PATENT DOCUMENTS

| | | | |
|---|---|---|---|
| DE | 2602939 | * | 7/1977 |
| EP | 0646352 A | | 4/1995 |
| JP | 63123543 A | | 5/1988 |

OTHER PUBLICATIONS

International Search Report dated Mar. 19, 2009 for International Appln. No. PCT/US2008/085311.

* cited by examiner

*Primary Examiner* — Edward Tolan
(74) *Attorney, Agent, or Firm* — Emil Richard Skula

(57) ABSTRACT

A method of mechanically treating alloy metal surgical needles to improve bending strength is disclosed. The needles are curved and reverse-curved in this method to improve bending strength.

7 Claims, 8 Drawing Sheets

FIG. 5
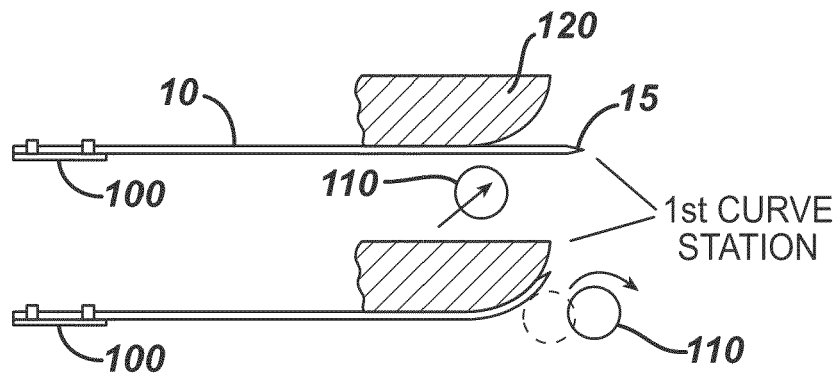
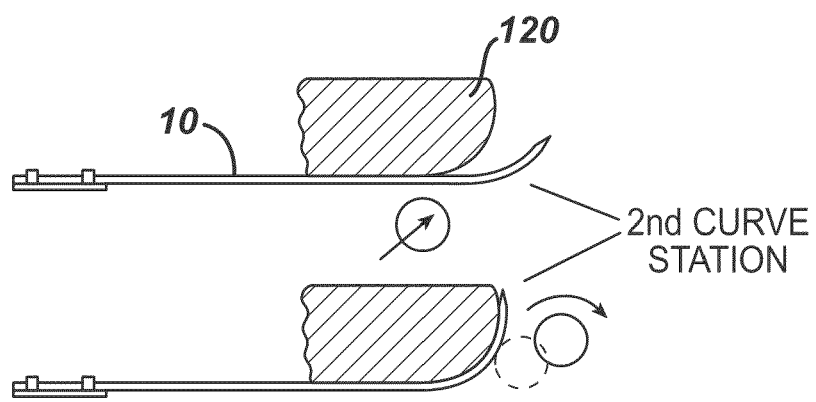
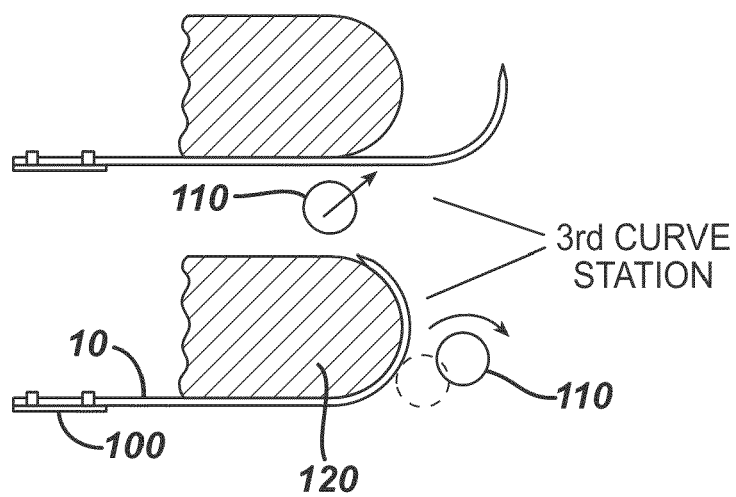

US 7,937,981 B2

PROCESS FOR TREATING METAL ALLOY SURGICAL NEEDLES TO IMPROVE BENDING STIFFNESS

FIELD OF THE INVENTION

The field to which this invention relates is surgical needles, in particular, methods of treating stainless steel and tungsten alloy surgical needles to improve mechanical characteristics.

BACKGROUND OF THE INVENTION

Surgical needles and methods of manufacturing surgical needles are well known in the art. Surgical needles are typically manufactured from biocompatible alloys such as 300 and 400 series stainless steels (stainless steel alloys), and the like. It is also known to manufacture surgical needles from polymeric materials, ceramics, and composites. Metal alloy surgical needles are manufactured using a variety of manufacturing processes. Typically, a metal alloy is drawn into a wire using a conventional wire drawing process using dies. The wire is then cut into discreet needle blanks. The needle blanks are the precursors of the surgical needles and undergo a series of conventional mechanical, thermal and chemical processes and treatments in order to be formed into a finished surgical needle suitable for mounting to a conventional surgical suture. The mechanical processes include straightening, curving, coining, grinding, and the like. The thermal processes include heat treating, age hardening, annealing and the like. The chemical processes include passivation, polishing, etching, coloring, and the like.

Surgical needles require a variety of requisite mechanical properties and characteristics in order to function optimally when used in surgical procedures. Since surgical needles and attached sutures are used to approximate or join tissue, these characteristics include ease of penetration through tissue, sharpness of needle points, stiffness, yield strength, ultimate strength, ductility, biocompatibility, etc.

There has been increased interest in this art for surgical needles having improved bending stiffness. Bending stiffness is particularly important for curved surgical needles so that a needle maintains its shape when subjected to forces as the surgeon moves the needle through tissue. Accordingly, there has been interest in this art to manufacture surgical needles from refractory alloy materials. Examples of such refractory alloy materials include tungsten rhenium alloys (W—Re). It is known that W—Re alloys exhibit exceptionally high Young's Moduli in excess of 400 GPa.

However, when formed into a curved suture needle this exceptional resistance to elastic deformation is reduced substantially. When an "unbending" moment is applied to the curved needle, plastic deformation initiates at relatively low applied stresses.

There have been numerous attempts to improve the bending stiffness of surgical needles. Although such approaches may have produced relative degrees of improvement, these approaches have not been shown to enhance the bending stiffness of W—Re surgical needles. For example, precipitation strengthened steel alloys have been used to maximize bending stiffness of ferrous needles. The configuration of surgical needles has been changed to incorporate various forms of rectangular geometries in order to gain an increase in bending stiffness. Another approach that has been used is the use of oversized large surgical steel needles with relatively small sutures to enhance stiffness in bending. Yet another way of attempting to improve bending stiffness is to select specific types of alloys with high moduli.

Accordingly, there is a need in this art for improved surgical needles made from metal alloys, in particular tungsten alloys, that are significantly stiffer than conventional curved stainless steel needles and which have improved characteristics in comparison to other tungsten alloy needles.

SUMMARY OF THE INVENTION

Therefore, a method for eliminating the negative effect of needle curving and substantially enhancing the stiffness in bending is disclosed.

The novel method of the present invention provides for mechanically treating tungsten or stainless steel alloy (collectively referred to as metal alloys) surgical needles to improve bending resistance is disclosed. In this method, a metal alloy needle is provided. The needle is formed into a first, initial curved configuration having a first radius. The needle is then substantially reverse-curved a sufficiently effective amount required to form the second curved configuration having a second radius, wherein the second radius is greater than the first radius thereby improving the bending stiffness properties of the finished curved needle.

Yet another aspect of the present invention is a surgical needle having improved properties treated with the above-described method.

As a consequence, surgeons may benefit from exceptional control and handling when using such metal alloy suture needles.

These and other aspects of the present invention will become more apparent by the following description and accompanying drawings.

BRIEF DESCRIPTION OF THE DRAWINGS

FIG. 5 illustrates a schematic of a typical progressive curving method.

DETAILED DESCRIPTION OF THE INVENTION

Figure 1:
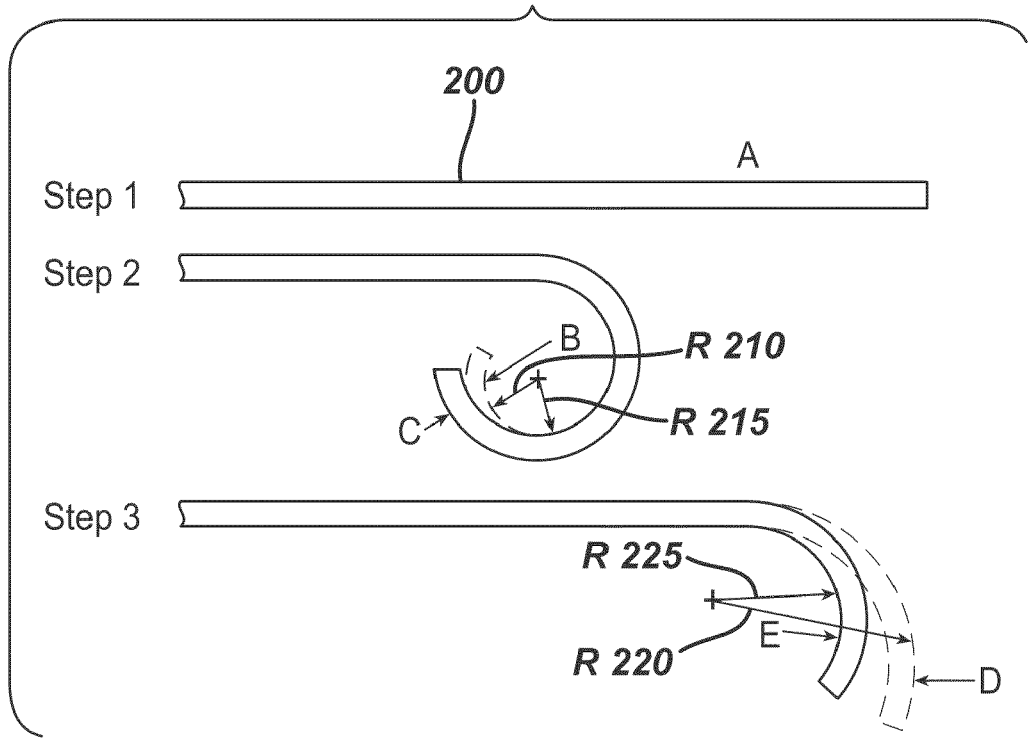
FIG. 1 illustrates a schematic of a mechanical curve stiffening process of the present invention referred to as an over-curve/reverse-curve process

The following terms used herein are defined to have the following meanings:
Dislocations—line defects in an atomic structure around which a mis-registry of atoms and strain field occurs.
Dislocation glide—motion of dislocations leading to the plastic deformation of the alloycurving—any process that transforms a straight surgical needle to one with a radius and arc length.

Over-Curving—any process that curves a straight surgical needle beyond it final desired radius and arc length Reverse-Curving—any process that transforms a surgical needle from an over-curved condition to the final desired radius and arc length Final Curve—the radius and arc length of a surgical needle conforming to the desired shape required for use Note: for any curving operation normal wire "springback" is expected; over-curving and reverse-curving need to account for this when being performed to achieve desired results. Metal Alloy—a substance composed of two or more metals Bending Stiffness (Stiffness in Bending)—resistance to elastic deformation of a curved suture needle.

Elastic Deformation—deformation, strain, or displacement that is recoverable by removing the applied load Rectangular Needle Body—any variety of needle body designs that incorporate flattened opposed sides (instead of an entirely rounded design, (could include square shape)

Martensitic Heat Treatment—Diffusionless transformation to convert austenite (crystal structure FCC) to Martensite (crystal structure BCT)

Maximum Bending Moment—the greatest moment applied to needle during bend test (ASTM standard F-1840-98a)

Precipitation Heat Treatment—heat treatment to form fine interdispersed precipitates of a second phase in a matrix of a first phase.

Precipitation Strengthened—describing heat treat history and properties that result Recrystallization Temperature—Temperature at which new grains will form in microstructure of an alloy within 1 hour.

Simple Tension—tension applied in one dimension with other dimensions being unconstrained.

Thermal Treatment—Application of thermal energy to incite an improvement in bending stiffness.

Yield Bending Moment or Surgical Yield Moment—the amount of moment required to initiate plastic deformation during needle bend testing (ASTM standard F-1840-98a)

Young's Modulus—The stiffness of a material (as measured by stress divided by elastic strain) in simple tension before the onset of plastic deformation Unbending Moment—The moment required to bend a curved suture needle against its curvature.

Materials Properties—Properties of the material only, derived by testing in a manner in which needle shape and surface properties do not influence data. Examples include: Young's modulus, ultimate tensile strength (when tested in simple tension), and microhardness.

Component Properties—Properties of the needle, which may result from a combination of material properties, needle shape, surface coatings, and testing methods The novel method of the present invention may be used to improve the bending resistance of a surgical needles made from a variety of metal alloys. The stainless steel alloys include, but are not limited to those which are substantially strengthened solely by work hardening (e.g. austenitic stainless steels), as well as the conventionally used 400-series and maraging stainless steels that are thermally processed prior to curving. Examples of refractory metals include alloys fabricated from tungsten, rhenium, molybdenum, niobium, and tantalum. Alloys of these elements, strengthened by cold drawing into wire and formed into curved surgical needles, would benefit from the present invention. It is particularly preferred to use tungsten-rhenium alloys, and more specifically tungsten 26% rhenium. The refractory metal alloys will typically be drawn into wire using conventional hot drawing processes well known in the art of refractory metal alloy manufacturing. A conventional tungsten alloy wire manufacturing process typically consists of the steps of producing fine tungsten and rhenium powders via refining of raw material compounds, typically ammonium para-tungstate and perenic acid, respectively. Next, consolidation and thorough mixing of tungsten and rhenium powders in the appropriate proportions is conducted to achieve the targeted alloy composition. The consolidated powders are pressed either via uniaxial or isostatic cold pressing to form an elongate rod or bar. The bar is then sintered at high temperature, e.g., typically in excess of 2400° C., to densify. Next the bar is subjected to high temperature (e.g., typically above 1500° C.) rotary swaging and continuous hot swaging to further elongate the bar or rod. Finally, the bar is subjected to a series of hot drawing steps typically above, e.g., approximately 700° C., to reduce the diameter of the bar to the desired wire diameter. Optionally, the wire is subjected to spin straightening, typically at an elevated temperature, but may be performed at room temperature as well.

It is also important to note that a variety of optional stress relieving heat treatments may be applied throughout this process to prevent excessive hardening of the material and thus enable further area reduction. Stress relieving heat treatments are typically performed below the recrystallization temperature of the tungsten alloy The wire sizes that are useful to produce surgical needles treated using the methods of the present invention will typically range from, but not be restricted to, 0.002 inch diameter to about 0.028 inch diameter. The wire size selected for a particular needle size and construction will depend upon user needs, particular surgical procedure, or the ability to attach a particular suture diameter. A wide variety of sizes and shapes are used for similar procedures, depending on preference and user technique.

Methods for manufacturing curved surgical needles are described in the for example in the following United States patents, which are incorporated by reference: U.S. Pat. Nos. 6,001,121A; 5,726,422A; 5,661,893A; 5,644,834A; 5,630,268A; 5,539,973A; 5,522,833A.

It is common knowledge in the art of small diameter wire processing, that a given length of wire can be curved or formed to a desired radius. The curving can be accomplished in a variety of operations or techniques. The curving process can be accomplished in single or multiple operations or stations.

A curved surgical needle allows the doctor to manipulate the needle through some media more efficiently than a straight needle. Different curvatures and length of curvatures are used on surgical needles to allow for flexibility and ease of use during surgery.

The following is a description of several curving methods known in the art which are useful in the practice of the present invention. The terms needle blank and surgical needle are used interchangeably in many instances herein. A needle blank is a term of art for a piece that is a pre-cursor to a finished surgical needle. The processes of the present invention may be used on needle blanks or finished surgical needles.

Figure 3:
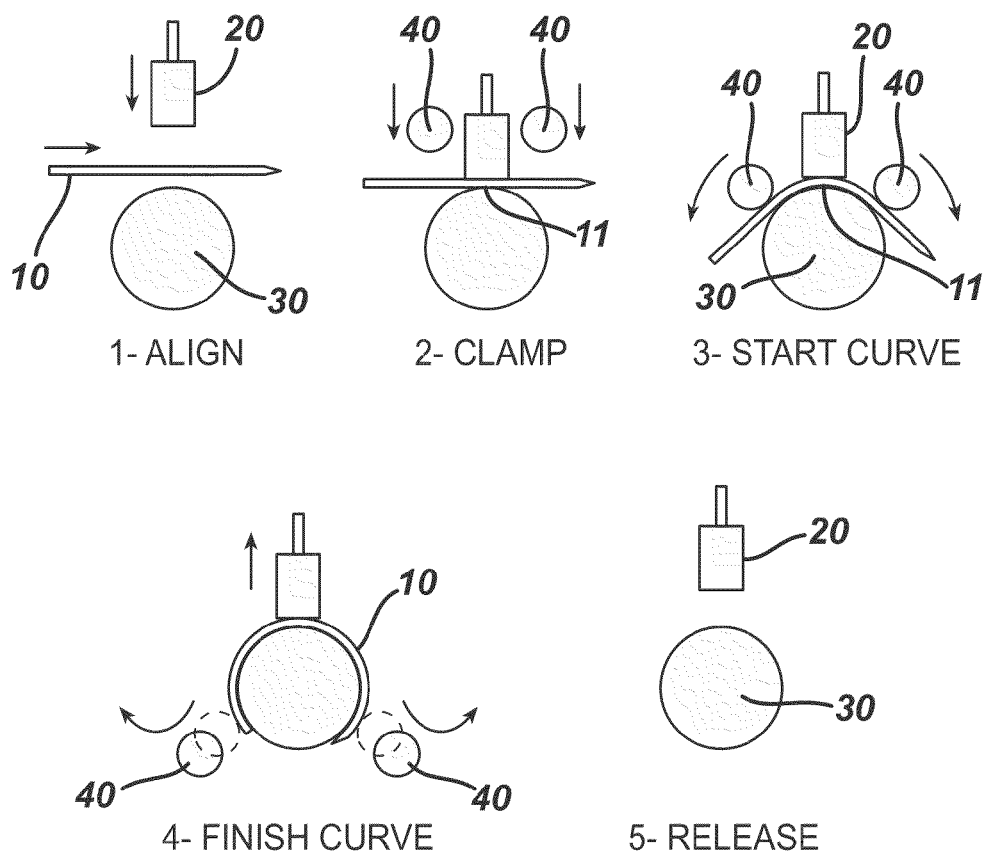
FIG. 3 illustrates a schematic of a typical dual arm curving method useful in the practice of the present invention.

Referring to FIG. 3, a dual arm curving method is illustrated (horizontal or vertical). Such a process is useful where a mostly finished needle has been formed, and curving would complete the mechanical processing. The remainder of the process steps, such as cleaning, heat treat, electropolishing, and siliconizing, can be handled in the "batch" mode, as the needle will be loose and randomly oriented at the completion of curving. A manufacturing chuck may be used to hand-off the needle blank to the feed mechanism. This chuck may be mounted in a rotary or linear arrangement. A surgical needle blank 10 is fed toward the curving mandrel 30 on a line about tangent to the mandrel's radius. The feed mechanism consists of a conventional gripper (not shown) which holds the needle blank 10. The gripper can be activated mechanically or pneumatically. After the needle blank 10 is positioned and secured in the gripper, it is fed toward the mandrel 30 by means of a conventional pneumatic cylinder (not shown). The cylinder feeds the needle blank 10 to a position that is tangent to the mandrel 30 with the tangent point being approximately the center 11 of the needle blank 10. The stopping position can be adjusted to compensate for different needle blank lengths. When the needle blank 10 is in the desired position (tangent to mandrel) a secondary pneumatic cylinder moves a holding pad (20), made from a suitable plastic, from a perpendicular direction. When the pad secures the needle blank 10, the gripper releases and returns to its initial position to allow for the next loading of a needle blank 10. The needle blank 10 which is being held between the mandrel 30 and pad 20, is now in the correct position for curving. The operating speed for this equipment will depend upon several parameters and may be for example between 20 and 300 parts per minute (ppm).

There are two mechanical rocker arms 40 on each side of the holding pad cylinder, each connected to conventional independent pneumatic cylinders (not shown), which drive the arms 40 toward the needle mandrel 30. Each arm 40 can have one or multiple rollers mounted in a position to facilitate the curving of the needle blank 10. The rollers can be manufactured from various materials such as teflon, nylon, or kevlar. A blend of such materials, with other known plastics and fibers, are commercially available. Fiberglass or kevlar reinforced resins or plastics are known for there long wearing properties. The size of the roller can vary, depending on the size of the radius to be curved, and generally is from about ⅛" to 1" in diameter. The distance the roller travels around the mandrel can be adjusted to curve completely around the needle blank 10 (full curve) or a lesser distance for a partial curve. As the rollers of arms 40 are driven toward the needle, and contact is made, the rocker arms 40 pivot in order to allow the rollers the opportunity to follow the mandrel 30 contour and curve the needle blank 10 to the desired curvature. The rocker arms 40 are spring loaded towards the mandrel 30, insuring the contour is followed.

After completion of the curving operation, the rocker arms 40 pivot so the rollers move away from the needle blank 10 to insure no contact with needle as the pneumatic cylinders retract. This action reduces the chance to damage the needle point (due to normal springback) when rollers of arms 40 return to initial home position. The holding pad 20 can release between the time that the rollers pivot away to the time the pneumatic cylinders retract the rollers. As the pad 20 releases, the curved needle blank is dropped into a hopper or onto a conveyor for disposition.

Figure 4:
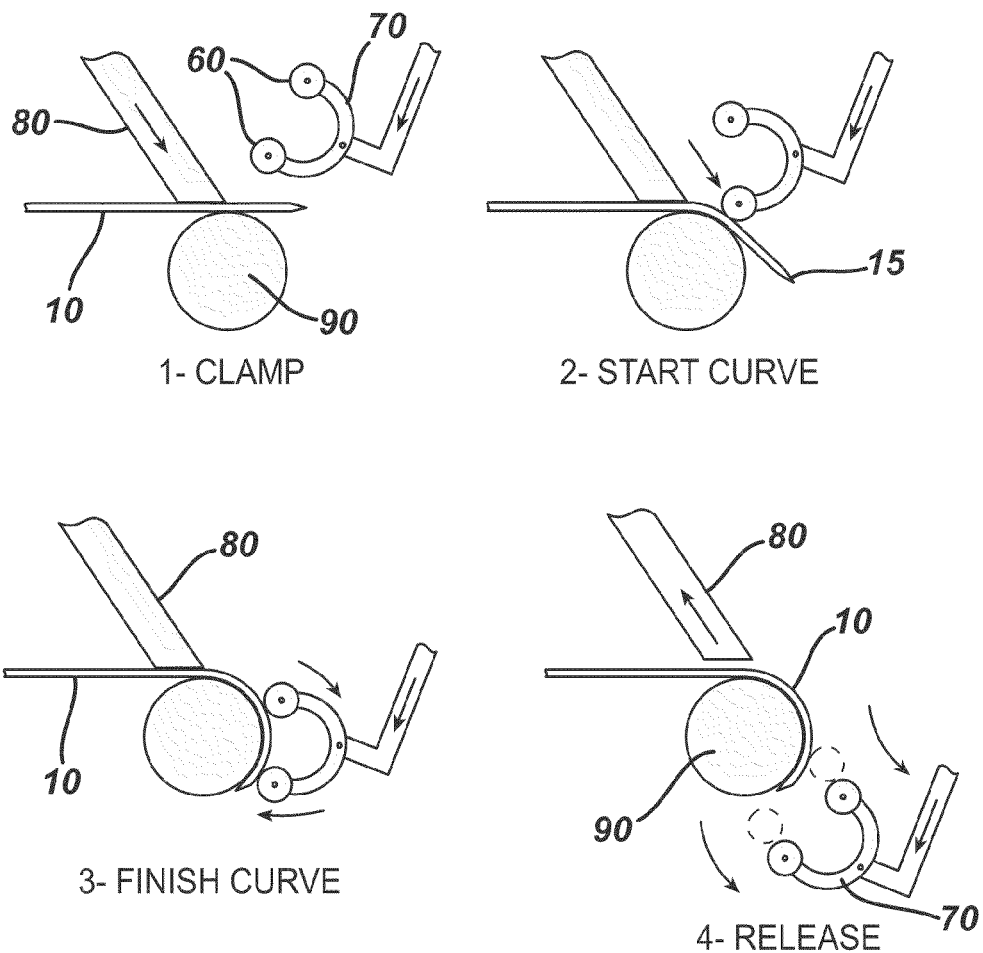
FIG. 4 illustrates a schematic of a typical curving method using the action of a single arm curver with a bogie roller.

FIG. 4 illustrates the action of a single arm curver with a bogie roller. In-line single arm curving (also known as bogie roller curving), is used where the needle blank is fed through the needle making equipment by means of a chucking system. The chucks which hold the needle blanks, are mounted to a metal band or roller chain, forming a conveyor that transports the chucks from one station to the next. Here, it is unnecessary to transfer the needle blank to another gripping device. The curving mechanism is in-line with other needle forming operations. The operating speed for this equipment may be between 10 and 300 ppm.

The curving operation is performed in one station where two rollers 60 are mounted to a pivoting bar 70, useful to curve the point area and body of the needle blank 10 in the same stroke. One roller 60 is constructed of a more forgiving material as discussed previously, and is used to curve the point/edge area of the needle blank 10 without damage. The other roller can be made of tool steel or carbide for body curving. Here, these harder materials yield a very long life.

As the needle blank 10 is fed into the curving position, a top slide unit, driven by cam (not shown), begins motion in the down direction. This motion allows an adjustable holding pad 80, made of tool steel or plastic like material, to come in contact with the needle, and holds or clamps the needle blank 10 to the curving mandrel 90. The curving mandrel 90 size will vary depending on the radius desired. The curving mandrel 90 is typically made from tool steel or carbide, although other materials may be used. After the clamping of the needle blank 10, the top slide continues downward and the "piggybacked" rollers 60 come into contact with the needle 10 and the curving mandrel 90. The rollers 60 pivot and follow the curving mandrel 90 contour. While following the contour, the rollers 60 curve the needle 10 around the curve mandrel 90. The lower roller 60 is for the point, and wraps around the needle blank 10 and curve mandrel 90, to a position that is sufficient to curve the point 15. The pivoting bar 70 is allowed to locate itself along the perimeter of the needle curvature. After curving, the pivot bar 70 is restrained and prevents roller 60 contact with the needle blank 10 on its retracting stroke, thereby preventing damage to the needle point 15 (again due to normal wire springback). The top slide unit returns to the up position, releasing the holding pad 80, completing the cycle.

Another conventional bending process involves curving a needle with walking beam equipment using a similar mechanism as the in-line method discussed above. In this method, the method of presenting the needle is different, causing some minor differences. In the methods described above, the needle blank is moved perpendicularly to its longitudinal axis, pauses while process "working" takes place, then advances again perpendicularly to the next station. In this example, the needle is likewise carried perpendicularly from one chuck to the next, however, after being secured in the chuck, the chuck moves the blank again, horizontally, this time parallel to the longitudinal axis of the needle blank, toward the working station. This presents a problem after curving, where the needle blank is wrapped around the mandrel. This is solved by pivoting the mandrel out of alignment with the needle before the retraction of the chuck occurs. Otherwise the mechanism is similar to the above example.

Another conventional method of curving needle blanks is known as progressive curving as illustrated in FIG. 5. As higher cycle speeds are needed to improve productivity, in general, complicated motions must be converted to simpler motions. To simplify the radial motion of the above type curving mechanisms, the work of curving needles can be reduced to approximately two or four, less complicated motions.

Typically in a high speed process, needle blanks 10 are mounted to carrier strips 100. The strips 100 move the needle blanks 10 to various processing stations. The curving of needle blanks 10 on carrier strips 100 can be performed on the needlemaking machine, or can be a "stand alone" operation on secondary equipment. The process of curving a needle blank 10 on a carrier strip 100 can be completed in one station or in multiple stations.

Referring again to FIG. 5, similar to the lower speed curving, the first station in the progressive curving process uses a nylon, teflon, or kevlar roller 110 (although other materials may be used) to curve the point section 15 of the needle blank 10. TA plastic roller 110 is preferably used so the cutting edges or point 15 of needle blank 10 are less likely to be damaged. Steel rollers 110 are used in the subsequent stations to complete the curve of the needle body. The steel body rollers 110 are form ground with a radiused or square relief in the profile, so the roller does not crush or distort the needle. The relief can be in the shape of a "V" as well, as in the case of a triangular body.

The process of curving is as follows. The bandolier or carrier strip 100 is fed by a mechanical feed system (not shown) to the desired position. The strip 100 can be pushed or pulled through the machine in a conventional manner, for example pulled by an index wheel attached to a cam driven shaft, or pushed through by a cam driven mechanical feed mechanism. When the needle is in position for curving, the rotation of cams (not shown) begin the decent of the curve mandrel blocks 120 towards the needle blank 10. This travel can be activated by a conventional overhead cam or a lower cam driving a mechanism attached to a connecting bar. At this point, if the needle blank 10 is rotatably held in the carrier 100, axial alignment should be insured for a proper curve. This can be done by aligning the "tail" of the needle blank, which has some fixed orientation with the needle itself.

The curve mandrel 120 is preferably adjusted so that it is approximately 0.001" from contact with the needle blank when the curve mandrel block 120 is in the full down position. This position can be referred to as bottom dead center. The bottom slide begins its upward motion. The curve rollers 110 come in contact with a lower roller plate (not shown), and roll on this plate before contacting the needle blank 10 just past the contact point of the upper mandrel 120. After contacting the needle blank 10, the curve roller 110 follows the curve mandrel 120 contour to curve the needle blank 10 to the desired radius and angle. After completion of the upward position, the cam that drives the tension arms begins to retreat which pulls the curve rollers 110 away from the needle blank to clear the needle as the curve rollers 120 return to the start position.

Each needle blank 10 can have one to four curving operations performed. The procedure is repeated in each curve station as the bandolier carrier 100 progresses until the curving of the needle blank 10 is complete. After curving, the needle blank 10 can be processed further with other equipment, since it is still attached to the carrier 100.

The novel methods of the present invention provide for increasing the stiffness of curved tungsten alloy suture needles in bending. In the method of the present invention, mechanical curving, then reverse-curving has been identified as a process that will substantially increase the stiffness of curved metal alloy suture needles without significantly decreasing their ultimate bending moment. A schematic of a method of the present invention is illustrated in FIG. 1. Progressive curving is employed and the method of choice using at least 3 curve steps. As seen in FIG. 1, the process begins with a substantially straight needle blank or needle 200 (position A). Then the blank 200 is curved around a specified diameter mandrel to an initial desired radius R 210 (position B) and curvature is produced. Normal wire springback causes the actual radius to be larger R215 than that of the mandrel (position C). The needle blank 200 is then progressively "uncurved" using a reverse procedure opening the radius to radius R' 220 (position D) and springback to radius R225 (position E) and curvature to the final desired shape. Those skilled in the art will appreciate that results will be optimized for a particular needle configuration and material by testing a range of radii and curvatures. A single curve, reverse-curve cycle will be sufficient to effectively increase the stiffness substantially. The number of cycles can be increased to almost any number; the limiting factor will be reshape ductility and/or process considerations. The types of curved configurations for needles that can be mechanically treated by the novel methods of the present invention include any type of single radius needles, or any type of multiple radii needle geometry.

Figure 8:
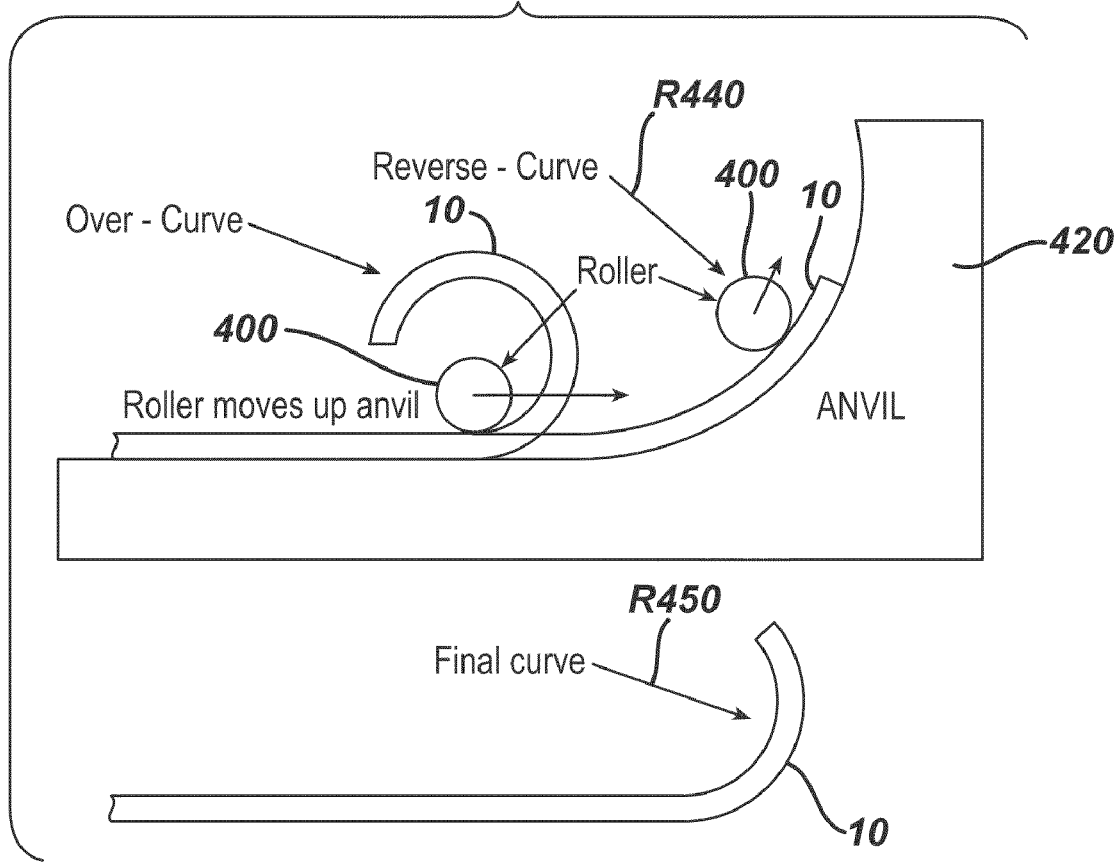
FIG. 8 illustrates a schematic of the reverse-curve process, showing the initial overcurve, a pin inserted that rolls the wire on the anvil, and the resulting final curvature.

Following the initial curve process of the present invention which results in an "over-curved" condition, the needle or blank 10 must be reverse curved to obtain the final desired curvature. As seen in FIG. 8, this is accomplished by placing a mandrel 400 (preferably steel) that has a diameter allowing it to fit inside the over-curved needle or blank 10, into the over-curved needle or blank 10 and rolling out the part against an anvil that has an internal radius R440. The internal radius R440 of the anvil is designed such that with either one or multiple rolls of the needle or blank 10, the resultant curvature after normal spring back will conform to the final desired curvature and radius R450, see FIG. 8 (Example 2)

An alternate method for reverse-curving is to apply a load to the over curved needle or blank such that the curvature opens enough for a larger mandrel to be placed within the needle or blank. Any standard method of mechanical curving previously described can now be used to reverse-curve the needle or blank to the final desired curvature and radius after allowing for normal spring back, see Example 1.

Stiffness in bending is an essential property for the handling and performance of suture needles. A compliant needle will deflect elastically during tissue penetration resulting in a loss of placement control. A stiff needle resists elastic deflection and can thus be directed as intended to provide a high level of control. Conventional suture needles achieve stiffness in a variety of conventional ways, including but not limited to providing a square or rectangular needle body, using large diameter wire from which to make needles, subjecting the needle to precipitation heat treatment, and subjecting the needle to martensitic heat treatment. The body of the suture needle may be formed into the shape of an I-beam to enhance the moment of inertia and stiffness of the needle, and it is similarly known to form the needle body into other high stiffness/high strength needle body designs.

Alternatively, for a given suture size, larger needle sizes may be used to attain higher stiffness in bending. However, large suture needles are more likely to cause tissue trauma and moreover, especially in cardiovascular application, leaking of blood from the larger puncture holes may result.

Finally, steel alloys, of special compositions that undergo precipitation strengthening after the needle is formed may be used. In these alloys, fine precipitates form throughout the microstructure and delay the onset of plastic deformation by pinning or inhibiting dislocation motion. Also, stainless steels such as AISI 420 are commonly used for surgical needles. Steels in this classification are strengthened by heat treatment, which involves microstructural phase change to martensite. Strength and hardness are increased, but elastic modulus is unaffected.

Suture needles are almost exclusively produced from stainless steels, and while all of the aforementioned techniques may be used to enhance needle strength, the needles are limited by the intrinsic stiffness or modulus of the steel material from which they are made. Some specialty needles may be produced from titanium, or Nitinol alloys, however, these alternative materials exhibit Young's moduli even lower than steel. To realize a substantial gain in suture needle stiffness over and above that attainable with steel alloys, it is necessary to use a different high modulus material.

Tungsten alloys exhibit exceptionally high stiffness along with other desirable physical properties. Considering only the theoretical Young's Modulus, tungsten alloys exhibit moduli in excess of 400 GPa, whereas steel alloys exhibit moduli of ~205 GPa. However, this substantial improvement in stiffness does not necessarily translate into an equivalent improvement in bending stiffness in finished curved surgical needles. Indeed, the conventional curving process during needle manufacture imparts stresses that act to reduce the bending stiffness of the curved suture needle. A method to rectify the negative effect of the curving process to realize exceptional stiffness in bending is needed. However, tungsten alloys that undergo precipitation hardening to enhance stiffness (described above) do not currently exist. Instead, it is believed that tungsten alloys derive their strength primarily from their high dislocation density and the natural resistance to deformation that occurs via dislocation—dislocation interaction as a stress is applied. The strength derived from dislocation—dislocation interactions is supplemented by solid solution strengthening wherein the strain field in the vicinity of rhenium atoms causes local distortions in the lattice of atoms that further resist the glide of dislocations responsible for plastic deformation of the alloy. During a standard needle curving process used in the manufacture of suture needles, the material at the outside radius of the needle is left with residual compressive forces while the material at the inside radius of the needle is left in a state of residual tension. In clinical use, when the needle experiences bending forces, plastic yielding will occur at a lower bending moment than the unprocessed material due to the presence of these residual stresses. In essence, these residual stresses, due to the curving process, detract directly from the compressive and tensile yield strengths of the material at the needle's outer and inner surfaces with the net result of a lower suture needle yield moment. It is believed that the multiple over-curve/reverse-curve processes described herein minimize, eliminate, or in extreme cases reverse the sign of these residual stresses located at the outer and inner surfaces. of the needle, thereby increasing the suture needle yield moment and effective bending stiffness.

The following examples are demonstrative of the principles of practice of the present invention.

EXAMPLE 1

In order to show the improvements in bending strength produced in refractory alloy surgical needles treated with the novel mechanical treatment process of the present invention, tungsten rhenium surgical needles were made in the following manner:

Wire was formed in a manner as described earlier in this disclosure. A needle blank was produced using conventional methods as described in the above-cited US patents.

The needle blanks were then mechanically treated in accordance with the novel method of the present invention in the following manner: Needles were curved to a radius of 0.129 inches; this being much smaller than the desired finished radius. The needles were then substantially reverse-curved to the desired radius of 0.373 inches.

Figure 2:
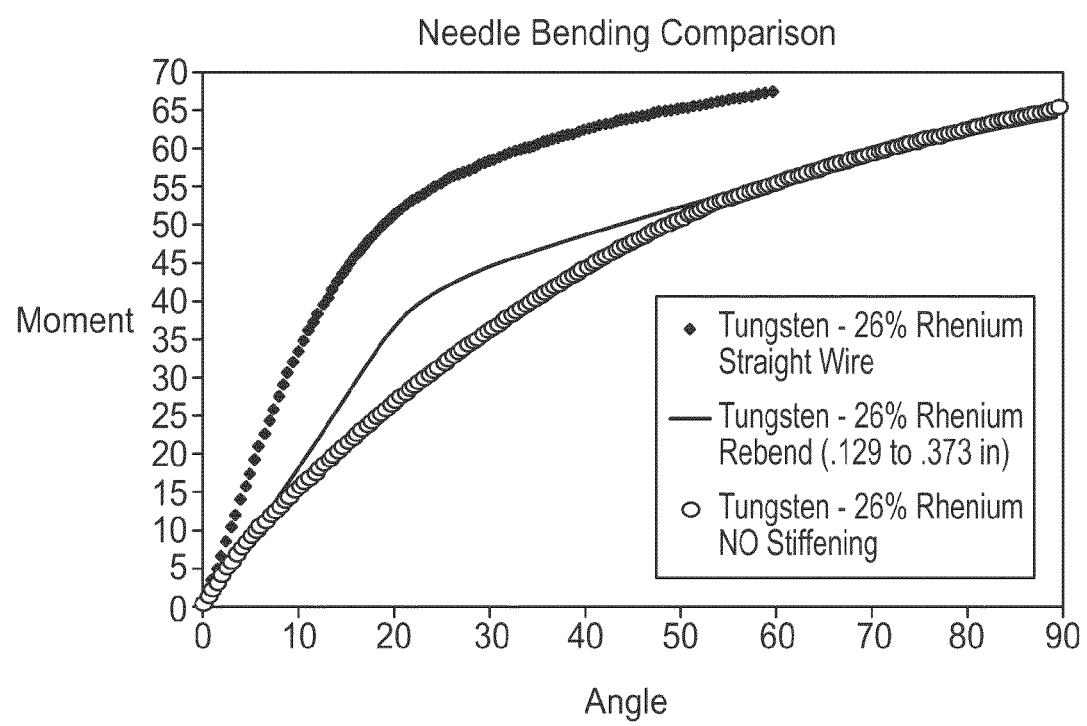
FIG. 2 is a graph of bending moment versus angle illustrating the results of the Over-Curve/Reverse-Curve sequence described in Example 1.

The effect of this treatment method on the bending performance of W-26% Re alloy curved suture needles (0.008" diameter) is shown in the graph of moment versus angle in FIG. 2.

Figure 6:
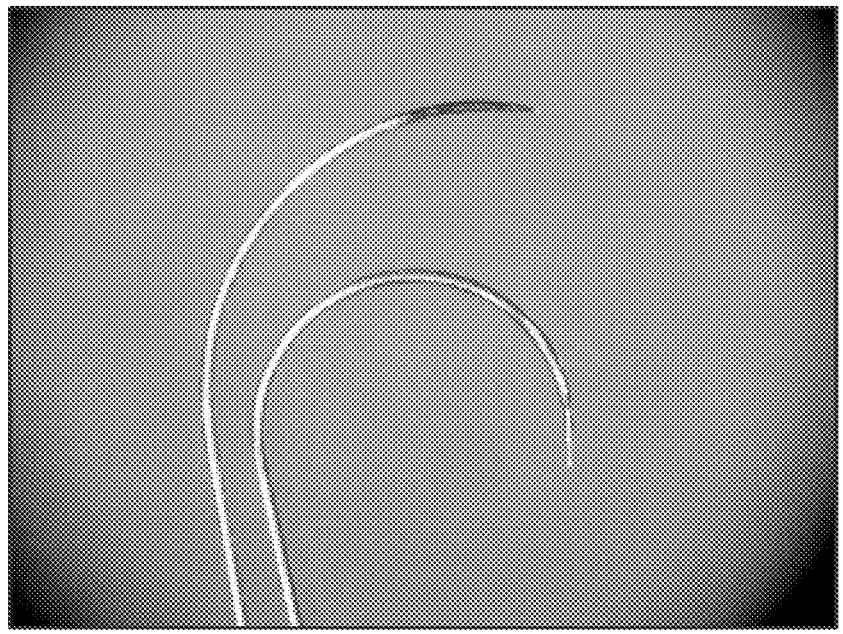
FIG. 6 is a photograph showing the actual needle curves of the curving sequence tested as described in Example 1 (0.129 inch radius to 0.373 inch radius).

The curves in FIG. 2 illustrate how the different initial curve radius impacted the final stiffness. FIG. 6 is a photograph showing the actual needle geometries resulting from the curving sequence (0.129 inch radius to 0.373 inch radius).

EXAMPLE 2

In this example all needles were curved to an initial radius in 3 or 4 progressive curving steps. They were curved using pins with a range of diameters from 0.100 inch to 0.190 inch. The curving rollers can be fabricated from plastic or steel. The "reverse-curving" step was performed with a small diameter steel roller, curving the needle open against a specified anvil having an internal radius which took into account normal wire springback and would result in the final desired needle curvature (see FIG. 8). This process can be accomplished with a variety of steps, anvil sizes and roller diameters, depending on the initial alloy, needle body geometry, initial curve, and final desired curve. The needles were made from W-26% Re needle blanks (0.008 inch diameter wire). The results are contained in the Table.

TABLE

| B<br>Init. Curve Pin<br>(diameter in.) | C<br>Init. Needle Rad.<br>(in.) | D<br>Fin. Reverse-<br>curve Anvil<br>(Radius in.) | E<br>Fin. Needle Rad.<br>(in.) |
| --- | --- | --- | --- |
| .100 | .066 | .295 | .155 |
| .148 | .109 | .245 | .155 |
| .190 | .155 | — | — |

Figure 7:
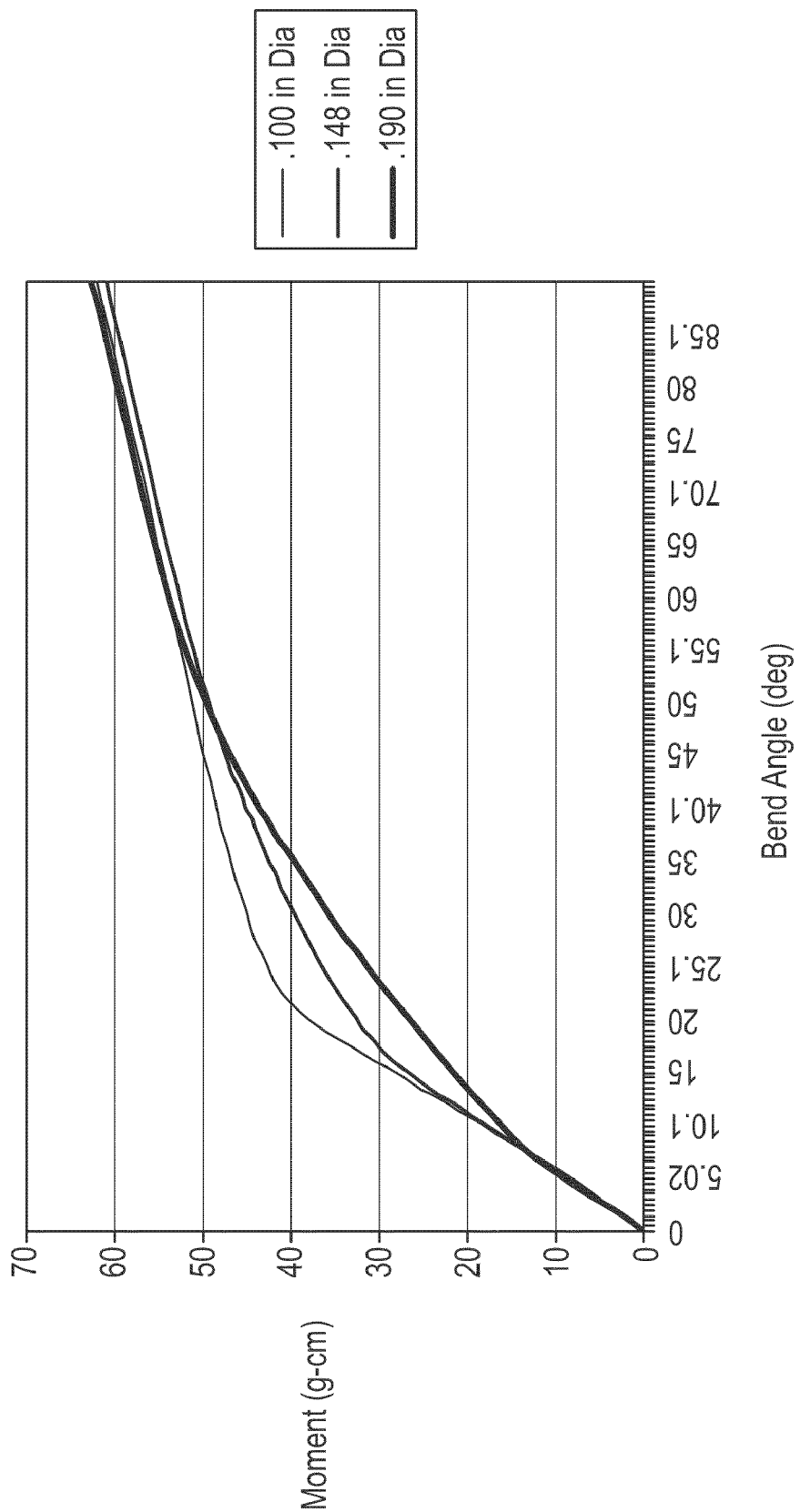
FIG. 7 is a graph of bending moment versus angle illustrating the impact of different initial radii (result of curving over different pin diameters) on the final bending stiffness using the over-curve/reverse curve method described in Example 2.

FIG. 7 is a graph of the data generated in this Example. The graph illustrates that needles made using the curve/re-curve method of the present invention exhibit substantial improvements in yield moment and stiffness per the definitions and descriptions provided in ASTM standard F-1840-98a. Moreover, no compromise in ultimate bending moment has occurred. It also demonstrates that by changing the initial over-curve radius, the final mechanical properties are impacted.

Although this invention has been shown and described with respect to detailed embodiments thereof, it will be understood by those skilled in the art that various changes in form and detail thereof may be made without departing from the spirit and scope of the claimed invention.

We claim:

1. A method of treating a metal alloy surgical needle, comprising:
   providing a metal alloy wire needle or blank, wherein the needle blank comprises a refractory metal alloy;
   forming the needle or blank into an initial curved configuration having a first radius; and,
   forming the needle or blank to a desired curved configuration by substantially reverse-curving the initial curved configuration into a final curved configuration having a second radius, wherein the second radius is greater than the first radius, and wherein the needle or blank has a reshape ductility,
   thereby improving the bending stiffness properties of the finished curved needle or blank.

2. The method of claim 1 wherein the needle blank comprises a tungsten-rhenium alloy.

3. The method of claim 1 wherein the surgical needle blank comprises a wire having a diameter between about 0.002 inches to about 0.060 inches.

4. The method of claim 1 wherein the surgical needle has a surgical suture attached thereto.

5. The method of claim 1 wherein ultimate bending moment of the suture needle is equal to or greater than the ultimate bending moment of an equivalent untreated suture needle.

6. The method of claim 2 wherein the reshape ductility of the tungsten-rhenium suture needle exceeds a value of 1.0.

7. A surgical needle, comprising:
a refractory metal alloy needle blank or needle, wherein the needle blank or needle is treated by the method of claim 1, thereby providing a needle or needle blank having improved bending stiffness.

* * * * *